United States Patent
McNamara

(10) Patent No.: US 8,741,303 B2
(45) Date of Patent: Jun. 3, 2014

(54) IMMUNOGENIC LHRH COMPOSITIONS AND METHODS RELATING THERETO

(75) Inventor: Michael Kerin McNamara, Alphington (AU)

(73) Assignee: Zoetis LLC, Florham Park, NJ (US)

( * ) Notice: Subject to any disclaimer, the term of this patent is extended or adjusted under 35 U.S.C. 154(b) by 0 days.

(21) Appl. No.: 13/587,249

(22) Filed: Aug. 16, 2012

(65) Prior Publication Data

US 2012/0328639 A1 Dec. 27, 2012

Related U.S. Application Data

(63) Continuation of application No. 13/167,438, filed on Jun. 23, 2011, now abandoned, which is a continuation of application No. 12/384,242, filed on Apr. 2, 2009, now abandoned, which is a continuation of application No. 11/027,683, filed on Jan. 3, 2005, now Pat. No. 7,534,441, which is a continuation of application No. 09/462,089, filed as application No. PCT/AU98/00532 on Jul. 9, 1998, now abandoned.

(30) Foreign Application Priority Data

Jul. 9, 1997 (AU) .................................. PO7768/97

(51) Int. Cl.
| | |
|---|---|
| A61K 39/385 | (2006.01) |
| C07K 7/06 | (2006.01) |
| C07K 14/33 | (2006.01) |
| C07K 14/59 | (2006.01) |
| A61K 31/721 | (2006.01) |

(52) U.S. Cl.
USPC .................. 424/185.1; 424/193.1; 424/278.1

(58) Field of Classification Search
None
See application file for complete search history.

(56) References Cited

U.S. PATENT DOCUMENTS

| | | | |
|---|---|---|---|
| 4,691,008 A | 9/1987 | Uhmann et al. | |
| 5,109,026 A | 4/1992 | Hoskinson et al. | |
| 5,324,512 A | 6/1994 | Ladd | |
| 5,378,688 A | 1/1995 | Nett et al. | |
| 5,403,586 A | 4/1995 | Russell-Jones et al. | |
| 5,573,767 A | 11/1996 | Dufour et al. | |
| 5,614,487 A | 3/1997 | Battersby et al. | |
| 5,684,145 A | 11/1997 | Van Der Zee | |
| 5,688,506 A * | 11/1997 | Grimes et al. | 424/184.1 |
| 5,885,966 A | 3/1999 | Meloen et al. | |
| 5,955,080 A * | 9/1999 | Reilly et al. | 424/194.1 |
| 6,013,770 A | 1/2000 | Reeves | |
| 7,534,441 B2 | 5/2009 | McNamara | |

FOREIGN PATENT DOCUMENTS

| | | |
|---|---|---|
| EP | 0 156 280 B1 | 2/1990 |
| GB | 2 228 262 A | 8/1990 |
| WO | WO 88/05308 A1 | 7/1988 |
| WO | WO 90/11298 A1 | 10/1990 |
| WO | WO 96/40755 A1 | 12/1996 |
| WO | WO 97/15316 A1 | 5/1997 |
| WO | WO 98/06848 A1 | 2/1998 |

OTHER PUBLICATIONS

Finnerty et al., J Reproduction and Fertility 101: 333-343, 1994.*
Prendiville et al., J Anim Sci 73: 2382-2389; 1995.*
Finnerty et al, J Reproduction and Fertility 101: 333-343, 1994.
Abaza et al., J of Protein Chemistry, 1992, pp. 433-444, vol. 11, No. 5.
Bowers et al., Endocrinology, Mar. 1980, pp. 674-683, vol. 106, No. 3.
Kaistha et al., Indian J. Pathiol Microbiol., Oct. 1996. pp. 287-292, vol, 39, No. 4.
Kuby et al., Immunology, Second Edition, 1994, pp. 86-96.
Ngo et al., The Protein Folding Problem and Tertiary Structure Prediction, 1994, pp. 492-495.
Singh et al., Biochem Int., Oct. 1991, pp. 509-520, vol. 25. No. 3.
Talwar et al., Int. J. Immunopharmacol., Apr. 1992, pp. 511-514, vol. 14, No. 3.
Ulker, H. et al., "The Effect of Immunization Against LHRH on Body Growth and Carcass Characteristics in Karakas Ram Lambs", Small Ruminant Research 45 (2002) 273-278.
Earl, Elizabeth R. et al., "Evaluation of Two GnRH-1 Based Vaccine Formulations on the Testes Function of Entire Suffolk Corss Ram Lambs", Vaccine 24 (2006) 3172-3183.
Government of Brazil, Ministry of Agriculture, Livestock and Procurement, Memorandum of May 3, 2007 Regarding Boar Taint.
J.A. Turkstra, et al., "Effects of GnRH immunization in sexually mature pony stallions", Animal Reproduction Science (2004), pp. 1-13.
R. J. Parkinson, et al., "A vaccination strategy for the long-term suppression of androgens in advanced prostate cancer", European Urology, 45 (2004) pp, 171-175.
T.A.E. Stout, "Suppressing reproductive activity in horses using GnRH vaccines, antagonists or agonists", Animal Reproduction Science, 82-83, pp. 633-643, 2004.

(Continued)

*Primary Examiner* — Phuong Huynh
(74) *Attorney, Agent, or Firm* — Barbara L. Renda; E. Victor Donahue

(57) ABSTRACT

The present invention relates generally to an immunogenic LHRH composition and more particularly to an immunogenic LHRH composition comprising a LHRH C-terminal fragment of at least five amino acids. The present invention is useful, inter alia, as a prophylactic and/or therapeutic agent for the modification of fertility and behavior patterns of animals, the achievement of livestock production gains such as increasing growth, decreasing feed conversion ratios or the control of unwanted organoleptic characteristics or the treatment of disorders of the reproductive organs.

3 Claims, No Drawings

(56) References Cited

OTHER PUBLICATIONS

C.A. Herbert and T.E. Trigg, "Applications of GnRH in the control and management of fertility in female animals", Animal Reproduction Science (2005), 88, pp. 141-153.

E. Fàbrega, et al., "Effect of vaccination against gonadotrophin-releasing hormone, using Improvac®, on growth performance, body composition, behaviour and acute phase proteins", Livestock Science 132 (2010) pp. 53-59.

C. Pauly et al., "Growth performance, carcass characteristics and meat quality of group-penned surgically castrated, immunocastrated (Improvac®) and entire male pigs and individually penned entire male pigs", Animal (2009), pp. 1-10.

W. T. Oliver et al, "A gonadotropin-releasing factor vaccine (Improvac) and porcine somatotropin have synergistic and additive effects on growth performance in group-housed boars and gilts", J Anim Sci (2003), 81:1959-1966.

C. Rikard-Bell et al., "Ractopamine hydrochloride improves growth performance and carcass composition in immunocastrated boars, entire boars, and gilts", J Anim Sci published online Jul. 31, 2009.

G. Zamaratskaia et al., "Effect of a Gonadotropin-releasing Hormone Vaccine (Improvac™) on Steroid Hormones, Boar Taint Compounds and Performance in Entire Male Pigs", Reprod Dom Anim, 43, pp. 351-359 (2008).

Casteels, M., Eeckhout, W., Beckaert, H. and Buysse, F., 1974. Suitability of boars for meat production. II. Odour and flavour of the meat. Landbouwtijdschrift, 27: 169-189.

Allen, P., Riordan, P.B., Hanrahan, T.J., and Joseph, R.L., 1981. Production and quality of boar and castrate bacon 1. Pig production, in-factory processing and carcass value. Irish Journal of Food Science and Technology, 5: 93-104.

Paschma, J., Plonka, S., Sabor, M., and Kolat, S., 1989. Comparison of daily gain, feed efficiency and carcass traits between young boars and castrates slaughtereed at various live weights. Roczniki-Naukowe-Zootechniki, 16, 143-153.

Campbell, R.G., Steele, N.C., Caperna, T.J., Solomon, M.B., and Mitchell, A.D., 1989. Interraltionships between sex and exogenous growth hormone administration on performance, body composition and protein and fat accretion of growing pigs. Journal of Animal Science, 67, 177-186.

Oeckel, M.J. van, Casteels, M., Warnauts, N., Boever, J.L. de, Renterghem, R. van, and Boucque, C.V., 1996. Production of entire males with Belgian Landrace and hybrid pigs: the incidence of sensory aberrations. Journal of Animal Physiology and Animal Nutrition, 76, 111-121.

Park, J.C., Kwon, O.S., Cho, K.H., Park, J.D., Kim, M.J., Park, M.K., Yoo, C.H. and, Lee, J.M., 1999. Effect of castration on body weight and carcass traits in pigs. Korean Journal of Animal Science, 41, 457-462.

Nadeje, B., Koucky, M., Sevrikova, S., Adamec, T., and Lastovkova, J., 2000. (Assessment of boar and barrow meat). Czech Journal of Animal Science, 45, 539-544.

Turkstra, J.A., Zeng, X.Y., Diepen, J.T.M., van, Jongbloed, A.W., Oonk, H.B., Wiel, D.F.M., van and Meloen, R.H., 2002. Performance of male pigs immunised against GnRH is related to the time of onset of biological response. Journal of Animal Science, 80, 2953-2959 . . . 55, 70, 98, 102.

Lawlor, P., Mullane, J., Lynch, P.B., Kerry, J., and Allen, P., 2003. Effect of sex and slaughter weight on production efficiency. Proceedings: EAAP Working Group on Production and Utilisation of Meat from Entire Male Pigs, Nov. 13-14, 2003, Teagasc, National Food Centre, Ashtown, Dublin 15, Ireland.

Dunshea et al, J Anim Sci; vol. 79, p. 2524-2535; Vaccination of boars with a GnRH vaccine (Improvac) eminates boar taint and increases growth performance; 2001.

R.E. Falvo, et al,: J. Anim. Sci. vol. 63: 986-994; Effect of Active Immunization Against LHRH or LH in Boars; Reproductive Consequences and Performance Traits; (1986).

G. Hagen, et al.: Effects of Immunization of Young Boars Against Gonadotropin Releasing Hormone; Proceedings of the XIth Congress on Animal Reproduction, (1988) (2), pp. 493-495.

X. Y. Zeng, et al.; Livestock Production Science; vol. 77: p. 1-11 (2002).

M. Bonneau, et al.: J. Anim. Sci: vol. 72: p. 14-20; The Effects of Immunization Against Luteinizing Hormone-Releasing Hormone on Performance, Sexual Development, and Levels of Boar Taint-Related compounds in intact male pigs; 1994.

Zeng, X.Y. et al.; Animal Reproduction Science; vol. 70, p. 223-233; Active immunization against gonadotrophin-releasing hormone in Chinese male pigs; 2002.

G. Killan, et al.; Amer. Journal of reproductive immunology; vol. 55, p. 378-384; Immunocontraception of Florida Feral Swine with a single-dose GnRH Vaccine; 2006.

G. Hagen, et al.; Proc. 11th Congress on Animal Production; Abstract 493; Effects of Immunization of Boars Against Gonadetropin Releasing Hormone; 1988.

A. Ladd, et al.; American J. Reproductive Immunology; 22: 56-63; Active Immunization against LHRH: Effects of Conjugation Site and Dose 1990.

S. Sad, et al.; Immunology; 74: 223-227; Carrier-induced Suppression of the antibody response to a self happen; 1991.

Meloen, et al.; Vaccine; 12: 741-746; Efficient Immunocastration of Male Piglets by Immunoneutralization of GnRH using a new GnRH-like Peptide; 1994.

C. A. Awonyl, et al.; J. Andrology; 9:160-171; Changes in Testicular Morphology in Boars Actively Immunization against Gonadotropin Hormone-Releasing Hormone; 1988.

A Van de Zee, et al.; Vaccine; 13: 753-758; P-fimbriae of *Escherichia coli* as carriers for gonadotropin releasing hormone; development of a recombinant contraceptive vaccine; 1995.

R. M. Hoskinson, et al.; Australian J. of Biotechnology; 4: 168-170; Vaxstrate: An Anti-reproductive vaccine for cattle; 1990.

I. S. Robertson, et al.; Vet Record; 111: 529-531; Effect of Immunological Castration on Sexual and Production Characteristics in Male Cattle; 1992.

I. A. Jeffcoate, et al.; Theriogenology; 18: 65-77; Effects of Active immunization of Ram Lambs and Bull Calves Against Synthetic Luteinizing Hormone Releasing Hormone; 1982.

A. Caraty, et al.; C. R. Acad. Sci. Paris; 303 Series III No. 16: 673-683; Endocrinologie; 1986.

* cited by examiner

IMMUNOGENIC LHRH COMPOSITIONS AND METHODS RELATING THERETO

The present application is a continuation of U.S. application Ser. No. 13/167,438, filed Jun. 23, 2011, now abandoned, which is a continuation of U.S. application Ser. No. 12,384, 242, filed Apr 2, 2009, now abandoned, which is a continuation of U.S. application Ser. No. 11/027,683 (now U.S. Pat. No. 7,534,441), filed Jan. 3, 2005, which is itself a continuation of U.S. application Ser. No. 09/462,089, filed May 1, 2000, now abandoned and which represents the U.S. national stage (35 USC section 371) of international application PCT/AU98/00532, filed Jul. 9, 1998. Priority is also claimed under 35 USC section 119 to Australian provisional application PO 7768/97, filed Jul. 9, 1997, the priority document for said PCT/AU98/00532 application. The complete text and disclosure of the Ser. No. 13/167,438 application is incorporated by reference herein, as if fully set forth.

The present invention relates generally to an immunogenic LHRH composition and more particularly to an immunogenic LHRH composition comprising a LHRH C-terminal fragment of at least five amino acids. The present invention is useful, inter alia, as a prophylactic and/or therapeutic agent for the modification of fertility and behaviour patterns of animals, the achievement of livestock production gains such as increasing growth, decreasing feed conversion ratios or the control of unwanted organoleptic characteristics or the treatment of disorders of the reproductive organs.

Bibliographic details of the publications referred to by author in this specification are collated at the end of the description. Sequence Identity Numbers (SEQ ID NOs.) for the amino acid sequences referred to in the specification are defined following the bibliography.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Vaccination against the hypothalamic hormone luteinising hormone releasing hormone (referred to herein as "LHRH", also known as GnRH) has been demonstrated as an immunological method of controlling reproduction since the early 1970s (Fraser 1975, Jeffcoate et al 1982). Eliciting an immune response to LHRH prevents the release from the anterior pituitary of the hormones LH and FSH, which are required for the development and maintenance of the gonads—the testes in the male and ovaries in the female. Thus reduction of LH and FSH levels leads to loss of reproductive function.

De-sexing (or neutering) operations are the most widely practised surgical procedures in veterinary medicine and livestock animal management. A significant proportion of both sexes of domestic livestock and companion animals are routinely surgically de-sexed to prevent a variety of undesirable characteristics which accompany sexual maturity. The traits include fighting, wandering, sexual behaviour, loss of condition, tumours of reproductive organs and pregnancy.

The control of mating behaviour by vaccination with LHRH-conjugate vaccines in companion animals such as dogs, cats and horses, and in livestock specifically in male pigs and male and female cattle, has been identified by the inventor as a goal as significant as the control of fertility.

Similarly, the control and treatment of disorders of the gonads and other reproductive organs, of both humans and animals, such as testicular cancer, breast cancer, prostate cancer, ovarian cancer, prostate enlargement or endometriosis is of significance.

The first published report of vaccination with an LHRH conjugate vaccine in rabbits showed that a dramatic effect was achieved in the development of the testes. Early reports of the application of an LHRH vaccine in pigs (Falvo et al, 1986, Caraty and Bonneau 1986), showed that effective formulations based on 1-10 LHRH conjugated to human serum globulin or bovine serum albumin could control testes development and hoar taint. Awonyi et al. (1988) showed that the effect of vaccination of pigs against LHRH affected primarily testis development. All these trials were done on small numbers of animals, with no reports of efficacy.

The problems of variability of LHRH-conjugate vaccines in controlling boar taint have been attempted to be overcome by genetically incorporating LHRH amino acid sequences into carrier proteins, including the pilin gene from $E.\ coli$ (Zee et al 1995) and into a truncated leucotoxin gene from $Pasteurella\ haemolytica$ (Potter et al 1997). These fusion proteins are produced as recombinant molecules and not by biochemical coupling. Trials have shown these recombinant proteins to function as immunocastration vaccines. However, they have not resulted in commercially available vaccines and press reports suggest less than desired efficacy.

In keeping with the less than perfect nature of highly developed and widely applied subunit vaccines for disease prevention, immunocastration vaccines based on specific LHRH-protein conjugates have also been shown to be less than perfect at inducing antibody to LHRH or in reducing hormones or other parameters associated with reproductive functions. There has been a general recognition of a wide variation in the effective induction of antibody to LHRH with a variety of LHRH-conjugate vaccines (Meloen et al 1994).

Vaccination of cattle with a 1-10 LHRH peptide—human serum albumin conjugate in Freunds adjuvant (Robertson et al, 1982), gave good antibody responses to LHRH after 2 vaccinations in only 5 of 10 vaccinated cattle. Even with boost vaccinations, the poor responders did not maintain antibody titres or have suppressed testosterone. A commercially developed vaccine for cattle (Vaxstrate), was only 80% effective (Hoskinson et al 1990).

Experiments in mice (Sad et al 1991) have shown that responses to LHRH-conjugates are genetically based. The vaccine was a 1-10 LHRH peptide, with the substitution of D-lysine instead of L-glycine at the 6 position, conjugated to diphtheria toxoid and adjuvanted with alum. Some strains of mice responded well, while others showed suppression of antibody to LHRH. These results would lead those skilled in the art of vaccine formulation to expect that a significant proportion of an outbred population would fail to respond or respond poorly to an LHRH-conjugate subunit type vaccine.

Vaccination of male pigs has resulted in variable suppression of testis development and suppression of boar taint. Bonneau and coworkers have shown (Bonneau et al 1994) that a 1-10 LHRH-α globulin conjugate given in oil emulsion for primary vaccination and saponin adjuvant for boost vaccination gave an antibody response in only 90% of 20 vaccinated pigs. Testosterone levels were suppressed in only 16/20 vaccinates (75%). Thus the quality as well as the amount of antibody is important in determining the efficacy of an LHRH-conjugate based vaccine. Hagen et al (1988) claimed that vaccination of 6 boars with an LHRH-bovine serum albumin (BSA) conjugate in Freunds adjuvant could reduce boar taint. However, 2/6 boars had low antibody responses and had normal spermatogenesis and testis function. Skatole levels were not affected by vaccination against LHRH.

Accordingly, there is a need to develop an LHRH vaccine which is consistently more highly effective than those utilized to date.

In work leading up to the present invention, the inventor has determined that the efficacy of vaccination against LHRH is significantly improved when LHRH is administered as a conjugate with diphtheria toxoid and an ionic polysaccharide.

Accordingly, one aspect of the present invention relates to a preparation for use in eliciting an effective immune response to LHRH, said preparation comprising a LHRH-diphtheria toxoid conjugate adsorbed to an ionic polysaccharide.

Reference to an "ionic polysaccharide" should be understood as a reference to any positively or negatively charged polysaccharide or derivative or chemical equivalent thereof. Reference to "derivative" and "chemical equivalent" should be understood to have the same meaning as outlined below. Said ionic polysaccharide may be in soluble or insoluble form. Preferably said ionic polysaccharide is an ionic dextran. Even more preferably said ionic dextran is DEAE-dextran, dextran sulphate or QAE-dextran. Most preferably, said ionic dextran is DEAE dextran. Preferably, the dextran component of said ionic dextran exhibits a molecular weight in the range 250,000 to 4,000,000 Da and even more preferably 500,000 to 1,500,000 Da.

According to this most preferred embodiment, the present invention relates to a preparation for use in eliciting an effective immune response to LHRH, said preparation comprising a LHRH-diphtheria toxoid conjugate adsorbed to DEAE-dextran.

Reference to an "effective" immune response should be understood as a reference to an immune response which either directly or indirectly leads to the reduction or complete blocking of reproductive function (i.e. reduces or prevents the functioning of any one or more of the reproductive organ's activities or modulates the hormonal levels of an animal such that any one or more aspects of reproduction or reproductive activity are reduced) in at least 90%, and preferably at least 95%, of animals treated. It should be understood that efficacy is a functional measure and is not defined by reference to anti-LHRH antibody titre alone since the presence of circulating antibody alone is not necessarily indicative of the capacity of said circulating antibody to block reproductive function. The term "reproductive organ" should be understood in its broadest sense to refer to the male and female gonads and accessory sexual organs. "Accessory sexual organs" should also be understood in its broadest sense and includes, for example, the prostate, breasts and the uterus.

Reference hereinafter to "LHRH" should be read as including reference to all forms of LHRH and derivatives thereof.

"Derivatives" include fragments, parts, portions, chemical equivalents, mutants, homologs and analogs from natural, synthetic or recombinant sources, including fusion proteins. For example, said LHRH includes peptides comprising a sequence of amino acids substantially as set forth in SEQ ID NO:1 or SEQ ID NO:2 or SEQ ID NO:3 or SEQ ID NO:4 or having at least 50% similarity thereto. The molecules defined in SEQ ID Nos:1, 2 and 3 are from the human and are conserved across all mammals. SEQ ID NO:4 is a derivative of SEQ ID NO:2 wherein spacers have been introduced at the N-terminus. Chemical equivalents of LHRH can act as a functional analog of LHRH. Chemical equivalents may not necessarily be derived from LHRH but may share certain similarities. Alternatively, chemical equivalents may be specifically designed to mimic certain physiochemical properties of LHRH. Chemical equivalents may be chemically synthesised or may be detected following, for example, natural product screening.

Homologs of LHRH contemplated herein include, but are not limited to LHRH derived from different phyla including birds, fish, reptiles and invertebrates.

"Derivatives" may also be derived from insertion, deletion or substitution of amino acids. Amino acid insertional derivatives include amino and/or carboxylic terminal fusions as well as intrasequence insertions of single or multiple amino acids. Insertional amino acids sequence variants are those in which one or more amino acid or non-natural amino acid residues are introduced into a predetermined site in the protein although random insertion is also possible with suitable screening of the resulting product. Deletional variants are characterised by the removal of one or more amino acids from sequence. Substitutional amino acid variants are those in which at least one residue in the sequence has been removed and a different natural or non-natural residue inserted in its place. Typical substitutions are those made in accordance with Table 1:

TABLE 1

Suitable residues for amino acid substitutions

| Original Residue | Exemplary Substitutions |
|---|---|
| Ala | Ser |
| * Arg | Lys |
| Asn | Gln; His |
| Asp | Glu |
| Cys | Ser |
| Gln | Asn |
| * Glu | Ala |
| * Gly | Pro |
| * His | Asn; Gln |
| Ile | Leu; Val |
| * Leu | Ile; Val |
| Lys | Arg; Gln; Glu |
| Met | Leu; Ile |
| Phe | Met; Leu; Tyr |
| * Ser | Thr |
| Thr | Ser |
| * Trp | Tyr |
| * Tyr | Trp; Phe |
| Val | Ile; Leu |

Key:
Amino acid residues marked with an asterisk indicate residues present in the mammalian LHRH sequence.

Examples of non-natural amino acids include, but are not limited to the D-isomers of said amino acids. "Additions" to amino acid sequences include fusion with other peptides, polypeptides or proteins.

Reference to diphtheria toxoid should be understood as a reference to all forms of diphtheria toxoid and derivatives thereof. The term "derivatives" has the same meaning as hereinbefore defined. Derivatives may include, for example, molecules comprising the diphtheria toxoid T cell epitopes or said T cell epitopes in isolation.

Preferably, said LHRH comprises an LHRH C-terminal fragment of at least five amino acids. Even more preferably, said LHRH comprises the amino acid sequence substantially as set forth in SEQ ID NO:2 and wherein the carboxyl terminus of said amino acid sequence is amidated. Said preferred LHRH is referred to herein as "LHRH 2-10 form".

According to this most preferred embodiment there is provided a preparation for use in eliciting an effective immune response to LHRH said preparation comprising a LHRH 2-10 form-diphtheria toxoid conjugate adsorbed to DEAE dextran.

In another preferred embodiment said LHRH comprises the amino acid sequence substantially as set forth in SEQ ID NO:4. Said preferred LHRH is referred to herein as "modified LHRH 2-10 form".

According to this preferred embodiment there is provided a preparation for use in eliciting an effective immune response to LHRH said preparation comprising a modified LHRH 2-10 diphtheria toxoid conjugate adsorbed to DEAE dextran.

Although not intending to limit the invention to any one method, said peptide may be synthesised by Fmoc chemistry and the resulting peptide coupled to the carrier protein diphtheria toxoid. Said coupling may be performed as described in Ladd et al 1990 or in Bonneau et al 1994, and the resulting conjugate of peptide and carrier protein (referred to herein as "peptide-conjugate") processed to be free of unbound peptide and other biproducts of conjugation. Such processing may be achieved by conventional dialysis or by ultrafiltration. The resulting peptide-conjugate is adsorbed to the ionic polysaccharide adjuvant.

Without limiting the present invention to any one theory or mode of action, administration of an effective amount of the LHRH preparation of the present invention induces a significantly more effective immune response against LHRH than the LHRH-carrier-adjuvant compositions described in the prior art. Said improved efficacy is observed when the immunogenic LHRH composition specifically comprises the carrier diphtheria-toxoid and an ionic polysaccharide adjuvant.

In another aspect of the present invention there is provided a pharmaceutical composition comprising a LHRH-diphtheria toxoid conjugate adsorbed to an ionic polysaccharide together with one or more pharmaceutically acceptable carriers and/or diluents.

Preferably said ionic polysaccharide is DEAE dextran.

Even more preferably said LHRH is the LHRH 2-10 form.

As used herein, the term "pharmaceutical" includes "veterinary".

The pharmaceutical forms suitable for injectable use include sterile aqueous solutions (where water soluble) or dispersions and sterile powders for the extemporaneous preparation of sterile injectable solutions or dispersion. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle sin in the case of diversion and by the use of surfactants. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption or delayed release of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying, the freeze-drying technique and the spray-drying technique which yield a powder of the active ingredients plus any additional desired ingredient from previously sterile-filtered solution thereof.

When the active ingredients are suitably protected they may be orally administered, for example, with an inert diluent or with an assimilable edible carrier, or they may be enclosed in hard or soft shell gelatin capsule, or compressed into tablets, or incorporated directly with the food of the diet. For oral administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such useful compositions is such that a suitable dosage will be obtained. Preferred compositions or preparations according to the present invention are prepared so that an oral dosage unit form contains between about 0.1 µg and 2000 µg of active compound.

The tablets, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; and a lubricant such as magnesium stearate. When the dosage unit form is a capsule, it may contain, in addition to materials of the above type, a liquid carrier. Various other materials may be present as coatings or to otherwise modify the physical form of the dosage unit. A syrup or elixir may contain the active compound, methyl and propylparabens as preservatives, and a dye. Of course, any material used in preparing any dosage unit form should be veterinarily pure and substantially non-toxic in the amounts employed. In addition, the active compound(s) may be incorporated into sustained-release preparations and formulations.

Pharmaceutically acceptable carriers and/or diluents include any and all solvents, dispersion media, coatings, antibacterial and antifungal agents, isotonic and absorption delaying agents and the like. The use of such media and agents for veterinarily active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. For administration to livestock it is particularly advantageous to use a multi-dose container linked to a repeating vaccination gun. Dosage unit form as used herein refers to physically discrete units suited as unitary dosages for the subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit for as hereinbefore disclosed. A unit dosage form can, for example, contain the principal active compound in amounts ranging from 0.5 µg to about 2000 µg. Expressed in proportions, the active compound is generally present in from about 0.5 µg to about 2000 µg/ml of carrier. In the case of compositions containing supplementary active ingredients, the dosages are determined by reference to the usual dose and manner of administration of the said ingredients.

Although not intending to limit the invention to any one theory or mode of action, the induction of an effective immune response against LHRH results in prevention of the release of the hormones LH and FSH from the anterior pituitary. Since these hormones are required for the development and maintenance of the gonads, reduction in the levels of these hormones leads to a decrease or loss of reproductive functions. The vaccinated animals are therefore effectively neutered resulting in the loss of characteristics associated with sexual maturity such as fighting, wandering, sexual behaviour, loss of condition, organoleptic characteristics, tumours of reproductive organs and pregnancy.

Accordingly, another aspect of the present invention relates to a method of eliciting, in an animal, an effective immune response to LHRH said method comprising administering to said animal an effective amount of LHRH-conjugate.

Reference to "LHRH-conjugate" should be understood as a reference to the LHRH preparation of the present invention.

Reference to "animal" should be understood as the reference to all animals including primates (e.g. humans, monkeys), livestock animals (e.g. sheep, cows, horses, donkeys, goats, pigs), laboratory test animals (e.g. rats, guinea pigs, rabbits, hamsters), companion animals (e.g. dogs, cats), captive wild animals (e.g. emus, kangaroos, deer, foxes), aves (e.g. chickens, ducks, bantams, pheasants, emus, ostriches), reptiles (e.g. lizards, snakes, frogs) and fish (e.g. trout, salmon). Said animal may be male or female.

In a most preferred embodiment, the present invention relates to a method of eliciting, in an animal, an effective immune response LHRH said method comprising administering to said animal an effective amount of LHRH-conjugate wherein said immune response inhibits the reproductive capacity of said animal.

Preferably said LHRH-conjugate is LHRH 2-10 form.

Reference to "inhibiting the reproductive capacity of an animal" should be understood as the partial or complete reduction of the functioning of any one or more of the reproductive organs's activities or modulation of said animal's hormonal levels such that reproductive activity, such as sexual activity, is reduced.

Inhibiting the reproductive capacity of an animal may result in a number of consequences such as, but not limited to, the castration of said animal or the reduction or elimination of characteristics associated with sexual maturity (for example, fighting, wandering, sexual behaviour, loss of condition, unwanted organoleptic characteristics, tumours of reproductive organs and pregnancy). "Castration" should be understood as a reference to the neutering of both male and female. Inhibiting the reproductive capacity of an animal may also result in the cessation of tumor cell proliferation (for e.g. prostate cancer cells, breast cancer cells, ovarian cancer cells or testicular cancer cells), inhibition or reversal of hyperplasia, such as prostate enlargement, endometriosis or inflammatory responses.

Accordingly, another aspect of the present invention relates to a method of castrating an animal said method comprising administering to said animal an effective amount of LHRH-conjugate.

Preferably said LHRH-conjugate is the LHRH 2-10 form.

Yet another aspect of the present invention relates to a method of regulating oestrus cycling in a female animal said method comprising administering to said animal an effective amount of LHRH-conjugate.

Preferably said LHRH-conjugate is the LHRH 2-10 form.

Reference to "regulating" should be understood in its broadest sense and includes, for example, inhibiting or delaying oestrus.

Still yet another aspect of the present invention relates to a method of inhibiting characteristics induced by the sexual maturation of an animal said method comprising administering to said animal an effective amount of LHRH-conjugate.

Preferably said LHRH-conjugate is the LHRH 2-10 form.

Reference to "inhibiting characteristics induced by the sexual maturation of an animal" should be understood as a reference to the reduction or complete elimination of any one or more physical and/or behavioural characteristics induced either directly or indirectly by sexual maturation. Said physical and/or behavioural characteristics include, for example, fighting, wandering, sexual behaviour, loss of condition, unwanted organoleptic characteristics, oestrus cycling, fertility, pregnancy and tumours of the reproductive organs. Accordingly, inhibiting said characteristics includes inhibiting sexual activity (for example preventing female cattle mounting other female cattle) preventing or delaying ovulation, reducing aggressive behaviour or reducing unwanted organoleptic characteristics such as boar taint. In a particularly preferred embodiment, said characteristics are aggression and sexual activity.

According to this preferred embodiment there is provided a method of inhibiting aggression in an animal said method comprising administering to said animal an effective amount of LHRH 2-10 form-conjugate.

In another most preferred embodiment there is provided a method of inhibiting sexual activity in an animal said method comprising administering to said animal an effective amount of LHRH-2-10 form-conjugate.

Vaccination with LHRH conjugate in male dogs and cats can be used to control unwanted behaviour, particularly aggression and the urge to roam. In female dogs and cats, the desired effects are control of fertility and of unwanted behaviour at the time of oestrus, commonly termed "in heat" or "in season". The unwanted behaviour in females includes increased fractiousness, marking of territories, wandering and other behaviours associated with oestrus.

According to this most preferred embodiment there is provided a method of inhibiting characteristics induced by the sexual maturation of cats and/or dogs said method comprising administering to said cat and/or dog an effective amount of LHRH-conjugate.

Most preferably said characteristics are aggression and roaming in male cats and/or dogs and fractiousness, marking of territory, wandering and oestrus behaviour in female cats and/or dogs.

In the thoroughbred horse industry, the racing of stallions is associated with difficulty in handling and ease and consistency of training. A large proportion of young colts are gelded and raised as castrates to make than more manageable. This does not appear to impact significantly on their racing potential. A vaccine to control unwanted behavioural problems would allow the full racing potential of male horses to be realised, with the added benefit of reversibility and so obtaining the genetic benefit as a stud animal after their racing career is over.

The racing of fillies and mares (female horses) is at its height in the spring and to some degree in the autumn in the temperate climates of the world. It is at these times of the year that horses come into season. This causes difficulties in training, handling and in uneven and poor racing performance. An LHRH vaccine to control oestrus would have a large and ready market in the horse racing industry. There are currently products based on hormone analogues available to control oestrus in racing fillies and mares. These are reported to have a lasting effect on the ability of treated mares to breed.

Accordingly, in yet another preferred embodiment there is provided a method of inhibiting characteristics induced by the sexual maturation of horses said method comprising administering to said horse an effective amount of LHRH-conjugate.

Most preferably said characteristics are aggression in colts and oestrus behaviour and uneven performance in mares.

In cattle, the unmanageable behaviour of bulls is well known. Aggression of bulls can be directed toward stockmen, inanimate objects such as fences and drinking troughs and can result in serious fighting between cattle. Thus in most beef producing countries, bulls destined for beef production are castrated while still calves, and the resulting steers are raised. The raising of steers in preference to entire males has a significant negative impact on production performance, but this is judged to be an acceptable, even necessary trade off over the raising of more docile steers.

Heifers are raised for beef production in the USA and in Australia. The cycling of heifers in feedlots causes significant production losses. The cycling heifer has a large increase in activity levels, resulting in poor or negative growth over the 5-7 days of the cycle. The heightened activity levels of heifers in oestrus impacts on other heifers in the same pen, so that the production performance of the entire pen of 50-100 animals is affected. In the USA heifers are fed a diet containing melengestrol acetate (MGA), a synthetic steroid, to control oestrus. In Australia, and other countries where hormonal feed supplements are prohibited, heifers are raised in feedlots without feeding of MGA, with poor production performance.

Accordingly, the immunocastration of livestock, although reducing or eliminating characteristics associated with sexual maturity, generally results in a negative impact on production gains on immunocastrated animals over uncastrated animals. This theory is based on the well established fact that entire animals grow considerably faster and more efficiently than castrated animals. However, the inventor has determined that administering the LHRH preparation of the present invention to livestock nevertheless results in the achievement of production gains. Reference herein to "production gains" includes but is not limited to an increase in final weight of livestock at slaughter, lowering of feed requirements for each kilogram of carcass weight gained, increasing growth rate of said livestock as compared to uncastrated livestock, improving the quality of meat derived from said livestock (for example, by controlling unwanted organoleptic characteristics of said meat) or decreasing stress levels of intensively housed livestock by reducing aggressive interactions of the intensively housed animals or, with respect to pigs, control of boar taint.

Accordingly, yet another aspect of the present invention relates to a method of achieving production gains in livestock said method comprising administering to said livestock an effective amount of LHRH-conjugate.

Preferably said production gain is the reduction or elimination of unwanted organoleptic characteristics of meat from male livestock.

The LHRH-conjugate may be administered to the livestock in a single-dose, for example a single administration of a slow or pulsatile release vaccine or in multiple doses.

Preferably said LHRH-conjugate LHRH 2-10 form.

Accordingly, there is provided a method of achieving production gains in livestock said method comprising administering to said livestock an effective amount of an LHRH 2-10 form-conjugate.

Preferably said production gain is the reduction or elimination of unwanted organoleptic characteristics of meat from male livestock.

The term "livestock" includes but is not limited to mammals such as pigs, cattle, sheep; captive wild animals such as deer; and aves such as emus or ostriches. Most preferably, said livestock are pigs and cattle.

According to this most preferred embodiment, there is provided a method of achieving production gains in pigs said method comprising administering to said pigs an effective amount of an LHRH 2-10 form-conjugate.

Preferably said production gain is the reduction or elimination of boar taint.

In another most preferred embodiment, there is provided a method of achieving production gains in cattle said method comprising administering to said cattle an effective amount of an LHRH 2-10 form-conjugate.

In animals, and particularly humans, vaccination with LHRH-conjugate can be used as a prophylactic or therapeutic treatment for disorders which are modulated directly or in directly by LHRH. These disorders include malignancies of cells which are regulated by LHRH or regulated by hormones which are themselves regulated by LHRH, for example, testicular cancer, breast cancer, ovarian cancer, prostate cancer and cancers of oncofoetal cells or cells which are induced to express oncofoetal antigens when malignancy occurs. These disorders also include non malignant proliferative disorders such as hyperplasias, for example, prostatic hyperplasia or endometrial hyperplasia. Without limiting the present invention to any one theory or mode of action, some tumor cells express receptors for reproductive hormones, the synthesis of which are regulated by LHRH. By vaccinating against LHRH it is possible to prevent the release of these hormones. The LHRH-conjugate of the present invention may also be used to neat or prevent disorders such as ovarian polycystitis, endometriosis and inflammatory conditions. Further uses of the LHRH-conjugate of the present invention include human fertility treatment based on modulation of the libido.

Accordingly, another aspect of the present invention relates to a method of inhibiting the growth of cells which are regulated directly or indirectly by LHRH said method comprising administering an effective amount of LHRH-conjugate.

Preferably said cells are human cells.

Reference to cell "growth" is a reference to the proliferation, differentiation or functional activity of said cell. Reference to cell growth which is "regulated directly or indirectly by LHRH" should be understood as a reference to cell growth which is regulated by LHRH itself or cell growth which is regulated by hormones other than LHRH which are themselves either directly or indirectly regulated by LHRH.

Reference to "inhibiting" should be understood as a reference to the prevention of cell growth, the cessation of cell growth or the down regulation of cell growth. Said cells may be located within the organ from which they derive or at some other location within the animal's body, such as, for example, where a malignant breast cell has metastasised in the liver.

In a particularly preferred embodiment said cells are malignant cells and most particularly malignant testicular cells, malignant breast cells, malignant ovarian cells or malignant prostate cells.

In yet another preferred embodiment said cells are hyperplastic cells such as prostatic hyperplastic cells or endometrial hyperplastic cells.

In yet another aspect of the present invention there is provided a method of down-regulating the libido of an animal said method comprising administering to said animal an effective amount of LHRH-conjugate.

Preferably said animal is a human.

Further features of the present invention are more fully described in the following Examples. It is to be understood, however, that this detailed description is included solely for the purposes of exemplifying the present invention. It should not be understood in any way as a restriction on the broad description of the invention as set out above.

EXAMPLE 1

Preparation of LHRH-Conjugate Composition

The LHRH-conjugate is based on a synthetic 2-10 form of Lutenising Hormone Releasing Hormone (LHRH) peptide coupled to a carrier protein. The peptide by itself is too small to be antigenic, and coupling to a carrier protein is required so that the peptide acts as a hapten and immunity is induced to LHRH. The carrier protein is diphtheria-toxoid.

The peptide is synthesised by Fmoc chemistry and the resulting 2-10 form LHRH peptide is coupled to diphtheria toxoid. The coupling may be performed as described in Ladd et al. 1990 or in Bonneau et al. 1994, and the resulting conjugate of peptide and diphtheria-toxoid processed to be free of unbound peptide and other by-products of conjugation. Such processing may be achieved by conventional dialysis or by ultrafiltration.

The resulting LHRH-carrier preparation may be used to prepare a composition for administration by formulation with or in an adjuvant (referred to as "LHRH-conjugate"). The adjuvant is an ionic polysaccharide such as DEAE-dextran, dextran sulphate or QAE-dextran. The adjuvant formulation may include a combination of two or more of the adjuvants listed. These lists are not to be taken as exhaustive. The selection of adjuvant is in part dependant on the species being targeted and is based on the level and duration of the immune response required and on the lack of reactogenicity (ie tissue compatibility). The level of active component and adjuvant are chosen to achieve the desired level and duration of immune response.

Formulations of LHRH-conjugate suitable for use in the present invention are preferably in range of 5-500 µg of LHRH-diphtheria toxoid in 5-500 mg of DEAE-dextran.

EXAMPLE 2

The LHRH vaccine (2-10 LHRH with diphtheria toxoid and DEAE dextran adjuvant as described in Example 1) was given to pigs as:

Group 1: 2 doses at 14 and 18 weeks of age, 10 male pigs per group.

Group 2: 3 doses at 14, 18 and 22 weeks of age, 10 male pigs per group.

Group 3: Controls received DEAE-dextran adjuvant alone, 10 male pigs per group.

Doses of LHRH vaccine were given subcutaneously. The LHRH vaccine is preferably in the range of 50-500 µg of LHRH-diphtheria toxoid in 50-500 mg of DEAE-dextran.

Pigs were slaughtered at 22 weeks of age (groups 1 and 3) or at 24 weeks (group 2).

Parameters measured:

Anti-LHRH titres were measured at 2 weeks post $2^{nd}$ dose.

Boar-taint compounds skatole and androstenone were measured in fat samples taken at slaughter.

Results:

Anti-LHRH titres 2 weeks post boost. Group mean tires are shown.

| Group | Titre |
|---|---|
| Group 1 | 4300 |
| Group 2 | 2760 |
| Group 3 | <20 |

* Boar taint compounds were measured in samples taken at slaughter.

Group mean values are shown.

| Group | Skatole* | Androstenone* |
|---|---|---|
| Group 1 | 0.06 | 0.18 |
| Group 2 | 0.05 | 0.23 |
| Group 3 | 0.07 | 0.51 |

*Boar taint compounds are expressed as µg/g fat tissue.

Conclusions:

The LHRH vaccine induced high levels of antibody in all vaccinated pigs as determined at 2 weeks post boost.

The LHRH vaccine was able to control boar taint compounds in all vaccinated pigs.

EXAMPLE 3

Mice 10 mice were vaccinated with formulations consisting of analogues of LHRH, linked to diphtheria toxoid and adjuvanted with DEAE dextran. Mice were vaccinated on days 0 and 14 and bled on day 21 to demonstrate induction of antibody to LHRH.

Analogues of LHRH tested in mice include:

```
2-10 LHRH:
                                          (SEQ ID NO: 2)
   His-Trp-Ser-Tyr-Gly-Leu-Arg-Pro-Gly-NH2.

Modified 2-10:
                                          (SEQ ID NO: 4)
   Gly-Ser-Gly-Ser-Gly-Leu-Arg-Pro-Gly-NH2.
```

Both constructs were linked to diphtheria toxoid by conventional chemistries. Mice received between 5-50 µg of conjugate per injection in 5-50 mg DEAE dextran adjuvant.

| LHRH-conjugate | titre 1 week post boost |
|---|---|
| 2-10-diphtheria toxoid | 3005 (n = 9) |
| Modified 2-10 | 1990 (n = 7) |

Titres to LHRH were induced in all mice vaccinated with the above constructs.

EXAMPLE 4

Cattle

Entire male and female cattle were vaccinated with a formulation comprising 2-10 LHRH conjugated to diphtheria toxoid, and adjuvanted with DEAE dextran. Cattle were 9-12 months of age at the time of initial vaccination. Each dose contained between 50 and 500 μg conjugate formulated in DEAE-dextran (50-500 mg).

Vaccinations were at 0 days with a boost vaccination at 28 days. Blood samples were taken at monthly intervals after the boost vaccination, and antibody titres measured by ELISA.

Female cattle (heifers) behaviour was monitored by daily inspection by trained farm staff and veterinarians. 8 weeks after boost vaccination, behaviour was also monitored by fixing of Heat Mount Detector pads (Kalmar Marketing Group Inc, Steamboat Springs, Colo., USA, dye releasing pads) to the rump of heifers. Mounting or riding behaviour (also called bulling) by cycling heifers will crush capsules of dye in the pads, which can be visualised from a distance. This usually only occurs when the standing heifer is receptive, ie in oestrus, and when the mounting heifer is also in oestrus. Thus the pads provide a useful continual monitor of oestrus in vaccinated heifers run with control unvaccinated heifers.

Results:
Anti-LHRH Titres.
GMT=Geometric Mean Titre of Group

| Vaccination Group | GMT 3 weeks post boost (range) | GMT 7 weeks post boost (range) |
|---|---|---|
| Placebo vaccinated controls | <100 | <100 |
| LHRH-diphtheria toxoid conjugate in DEAE dextran adjuvant | 10,357 (3623-26133) | 3435 (1538-15464) |

Riding Behaviour/Pad Reactivity:

Control heifers (female cattle) exhibited riding behaviour at the time of primary and boost vaccination and during the first 7 weeks after boost vaccination. None of the vaccinated cattle exhibited the behavioural patterns associated with reproductive function in cycling heifers. Scoring of cycling behaviour by direct observations were confirmed by Heat Mount Detector Pads, none of which were activated in vaccinates during the 7 week post boost period.

These results confirm the ability of the preferred formulation vaccine to modify behaviour of vaccinated animals, in this example the control of oestrus and associated behaviours in female cattle (heifers).

EXAMPLE 5

Dogs

Beagle/Foxhound cross dogs and bitches were vaccinated with a formation comprising 2-10 LHRH conjugated to diphtheria toxoid, and adjuvanted with DE dextran. Dogs were 6-10 months of age at the time of initial vaccination. Control dogs were not vaccinated.

Vaccinations were at 0 days with a boost vaccination at 28 days. Blood samples were taken at monthly intervals after the boost vaccination, and antibody titres measured by ELISA.

The dose of vaccine is preferably in the range of 50-500 μg LHRH-diphtheria toxoid in 10-100 mg DEAE-dextran.

Titres to LHRH in Dog Serum:

| Weeks post boost vaccination | Vaccinated with LHRH vaccine | Unvaccinated controls |
|---|---|---|
| 0 | <100 | <100 |
| 4 | 84,640 | <100 |
| 8 | 38,919 | <100 |
| 12 | 7,900 | <100 |

All titres shown are Geometric Mean Titres of the group of 7-8 dogs. Titres were measured by ELISA.

The data show that the favoured formulation of 2-10 LHRH conjugated to diphtheria toxoid in DEAE-dextran adjuvant induces a strong antibody response in 100% of vaccinated dogs. Of significance in this example is the demonstration that the preferred formulation is able to give duration of the antibody response.

Inhibition of Development of Testes:

At 16 weeks post boost, testes sizes were measured in controls and vaccinates, by reference to orchidometer beads.

Testes Size (Group Mean Values):

| Weeks post boost vaccination | Vaccinated with LHRH vaccine | Unvaccinated controls |
|---|---|---|
| 16 | 0.5 cm$^3$ | 12 cm$^3$ |

These data demonstrate that the preferred formulation is able to prevent the development of reproductive organs, as shown in this example in the inhibition of the growth and maintenance of testes in dogs.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Awonyi, C. A., Chandrashekar, V., Arthur, R. D., Schanbacher, B. D, and Falvo, R. E. *J. Androl.* 9:160-171 (1988).

Bonneau, M., Dufour, R., Chouvet, C., Roulet, C., Meadus, W. and Squires, E. J., *J. Animal Science* 72: 14-20 (1994).

Caraty, A. and Bonneau, M. *C.R. Acad. Sci. Paris* 303 Series D:673-683 (1986).

Falvo, R. E., Chandrashekar, V. et al. *J. Animal Science* 63: 986-994 (1986).

Fraser, H. M. *Immunization with Hormones in Reproductive Research:* 07-116 (1975).

Hagen, G., Andresen, O., Blichfeldt, T. and Berg, K. A. *Proc.* 11*th Congress on Animal Production Abstract* 493 (1988).

Hoskinson, R. M., Rigby, P. E., Mattner, V. L., Huynh, D'Occhio, M. D., Neish, A., Trigg, T. E., Moss, B. A., Lindsey, M. J., Coleman, G. D. and Schwartzkoff, C. L. *Aust. J. Biotechnol.* 4:166-170 (1990), Jeffcoate, L. A., Lucas, J. M. and Crighton, D. B. *Theriogenology,* 8:65-77 (1982).

Ladd A., Tsong Y. Y., and Than R. B., *American J. Reproductive Immunology* 22: 56-63 (1990).

Meloen, et al., *Vaccine* 12: 741-746 (1994).

Potter, A. A. and Manns, J. G. Patent—International filing number PCT/CA97/00559 (1997).

Robertson, I. S., Fraser, H. M., Innes, G. M. and Jones, A. S. *Vet. Record* 111:529-531 (1982).

Sad S., Gupta H., Talwar G. P., and Raghupathy R., *Immunology* 74:223-227 (1991).

Zee, A., Noordegraaf, C. V., Bosch, H., Gielen, J., Beremans, H., Hoekstra, W. and Die, I. *Vaccine* 13:753-758 (1995).

---

The invention claimed is:

1. A method of controlling reproductive behavior in cattle comprising administering to said cattle, in two doses, a vaccine composition comprising an LHRH-diphtheria toxoid conjugate adjuvanted with DEAE dextran, wherein the amino acid sequence of said LHRH is SEQ ID NO:2, and wherein the male cattle are 9-12 months of age at the time of first vaccination, and the second vaccination is provided at about 28 days following the first vaccination.

2. The method of claim 1, wherein the carboxy terminus of the LHRH amino acid sequence is amidated.

3. The method of claim 1, wherein each dose of vaccine composition provides between 50 and 500 micrograms of LHRH-diphtheria toxoid conjugate, and between 50 and 500 milligrams of DEAE-dextran.

* * * * *

SEQUENCE LISTING

```
<160> NUMBER OF SEQ ID NOS: 4

<210> SEQ ID NO 1
<211> LENGTH: 10
<212> TYPE: PRT
<213> ORGANISM: Homo sapiens

<400> SEQUENCE: 1

Glu His Trp Ser Tyr Gly Leu Arg Pro Gly
1               5                   10

<210> SEQ ID NO 2
<211> LENGTH: 9
<212> TYPE: PRT
<213> ORGANISM: Homo sapiens

<400> SEQUENCE: 2

His Trp Ser Tyr Gly Leu Arg Pro Gly
1               5

<210> SEQ ID NO 3
<211> LENGTH: 8
<212> TYPE: PRT
<213> ORGANISM: Homo sapiens

<400> SEQUENCE: 3

Trp Ser Tyr Gly Leu Arg Pro Gly
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ser Gly Ser Gly Leu Arg Pro Gly
1               5
```